(12) United States Patent
Malak

(10) Patent No.: US 8,118,032 B2
(45) Date of Patent: Feb. 21, 2012

(54) RAPID CRYO-HEATING DEVICES AND THEIR APPLICATIONS

(75) Inventor: Henryk Malak, Ellicott City, MD (US)

(73) Assignee: American Environmental Systems, Inc., Ellicott City, MD (US)

( * ) Notice: Subject to any disclaimer, the term of this patent is extended or adjusted under 35 U.S.C. 154(b) by 1186 days.

(21) Appl. No.: 11/186,008

(22) Filed: Jul. 21, 2005

(65) Prior Publication Data

US 2005/0283145 A1 Dec. 22, 2005

(51) Int. Cl.
*A61B 19/00* (2006.01)
(52) U.S. Cl. .......................................... 128/898; 607/88
(58) Field of Classification Search .................. 128/898; 606/2–26; 607/88–94
See application file for complete search history.

(56) References Cited

U.S. PATENT DOCUMENTS

| | | | | |
|---|---|---|---|---|
| 5,177,970 A | * | 1/1993 | Chang | 62/3.1 |
| 5,447,032 A | * | 9/1995 | Epstein et al. | 62/3.1 |
| 5,626,020 A | * | 5/1997 | Sangster et al. | 62/3.1 |
| 5,803,082 A | * | 9/1998 | Stapleton et al. | 600/407 |
| 5,963,680 A | * | 10/1999 | Kleinerman | 385/12 |
| 6,041,610 A | * | 3/2000 | Edwards et al. | 62/264 |
| 6,050,990 A | * | 4/2000 | Tankovich et al. | 606/9 |
| 6,537,829 B1 | * | 3/2003 | Zarling et al. | 436/514 |
| 2002/0174660 A1 | * | 11/2002 | Venkatasubramanian | 62/3.7 |
| 2004/0065655 A1 | * | 4/2004 | Brown et al. | 219/428 |
| 2004/0169468 A1 | * | 9/2004 | Peng | 313/512 |
| 2005/0169348 A1 | * | 8/2005 | Chen et al. | 374/161 |
| 2007/0131954 A1 | * | 6/2007 | Murayama et al. | 257/98 |

OTHER PUBLICATIONS

Laser-induced fluorescent cooling of rare-earth-doped fluoride glasses; Murtagh et al.; Journal of Non-Crystalline Solid, vol. 253 (1999) 50-57.*
Structural kinetics of laser-excited metal nanoparticles; Pleach et al., Chemical Physics, vol. 299 2004, pp. 183-191.*

* cited by examiner

*Primary Examiner* — Ahmed Farah

(57) ABSTRACT

This invention discloses cryo-heating devices and methods for cooling and heating objects in a very rapid timescale, from femtosecond to subsecond. The cryo-heating device comprising of an up-converting electromagnetic energy medium and an electromagnetic source that is further supported by another radiation source selected from the group of sonic, magnetic, electric, electroluminescent, up-converted luminescence, pressure and thermal. The medium in the cryo-heating phototreatment device is cooling or heating objects by up-conversion of electromagnetic energy and by conversion of electromagnetic energy, respectively. Both, cooling and heating of objects are achieved by electromagnetic radiation at different wavelengths, or at the same wavelength when objects are also absorbing electromagnetic radiation. The invention also proposes a further enhancement of cooling and heating of objects by the use of surface plasmon resonance conducting nanostructures embedded into the medium. The proposed devices and methods of very rapid cooling and heating can be applied in biomedical technologies and health care. The invention also includes applications of the disclosed herein method to up-conversion energy cooling of electronic components and photon detector devices.

4 Claims, 12 Drawing Sheets

RAPID CRYO-HEATING DEVICES AND THEIR APPLICATIONS

STATEMENT REGARDING FEDERALLY SPONSORED RESEARCH

There is NO claim for federal support in research or development of this product.

FIELD OF THE INVENTION

This invention is related to rapid cooling and heating devices and method of their use in electronics, biotechnology, medicine, and in human and animal therapy.

BACKGROUND OF THE INVENTION

There is a great need for methods and devices that can perform cooling and heating on a very rapid (subsecond) time scale. Such rapid thermocycling techniques would find applications in polymerase chain reaction (PCR) techniques for fast amplification of genetic materials. Current PCR devices and methods require several hours to obtain enough amplified genetic materials for further analysis. In times of terrorist threats, possible attacks with weapons of mass destruction (WMD), or in a case of any disaster, there is need for rapid medical responses in a variety of scenarios, where biochemical information is often required within minutes or even seconds.

The heating of objects can be performed very quickly by electromagnetic radiation and other thermal means. However, cooling objects to ambient temperature or below ambient temperature requires more time. Common cooling sources used for cooling objects are thermoelectrical devices based on the Peltier effect. These devices are not energy-efficient and cooling of objects is often much slower than required.

Another great need, particularly useful in the PCR technique, is non-contact heating and/or non-contact cooling. Non-contact heating of objects can be performed relatively easily and fast by various means including electromagnetic radiation, but means for very efficient non-contact cooling of objects do not exist. The pressure air-cooling technique is currently one of the solutions for non-contact cooling, but in use this technique is neither fast nor convenient enough.

Another great need for fast cooling and heating exists in therapeutic devices, such as acupuncture devices or other therapeutic devices that through bioactive treat the body. Nerve reactions and many other physiological processes occur on subsecond scale and therapeutic devices with thermocycling rates within this time scale would have great therapeutic value. Sports medicine also would greatly benefit from cooling-heating devices, which can be worn over the injured site to shorten the time of healing.

New techniques are also needed for cooling the backs of high-performance integrated circuits (ICs), which could allow for denser packaging of chips, while providing better temperature control and improved reliability. As the power density of high-performance integrated circuits increases, cooling of integrated circuits has become more significant concern. Conventional cooling techniques, which depend on heat sinks on the backs of ICs to transfer heat into streams of forced air, will be unable to meet the needs of future power-hungry devices—especially 3D multi-chip modules that will pack more processing power into less space.

SUMMARY OF THE INVENTION

This invention discloses cryo-heating devices and methods for cooling and heating of objects on a very rapid scale. The cryo-heating device comprising of: an up converting energy medium and an electromagnetic source that can be further supported by another radiation source selected from the group of: sonic, magnetic, electric, electroluminescent, luminescence, pressure, and thermal. The electromagnetic source in the cryo-heating device induces both cooling and heating processes in the medium by irradiating the medium with electromagnetic energy. Cooling of the medium is accomplished by up-conversion of electromagnetic energy absorbed by the medium that is associated with cooling of the medium and cooling of objects placed nearby or in direct contact with the medium. The processes of up-conversion-cooling of the medium and objects occurs in a very short time scale, from femtoseconds to sub-seconds. Heating the medium and subsequently heating objects is accomplished by irradiating the medium with electromagnetic energy at wavelengths that are absorbed by the medium, and do not cause up-conversion energy in the medium. Electromagnetic energy at these wavelengths or other additionally selected wavelengths may also be absorbed by objects causing instantaneous heating of objects.

The proposed cryo-heating device and method of very rapid cooling is very much needed in biotechnology, health care, and electronics.

The invention also sets forth a method for further enhancement of up-conversion cooling and/or heating processes in the medium by surface plasmon resonance (SPR) conducting nanostructures. To achieve enhancement, the nanostructures are placed into or nearby the up-converting medium, where they are irradiated by electromagnetic energy. The invention also considers the use of plurality wavelengths for cooling and heating of the medium and objects.

The cryo-heating device is proposed for use in biotechnology, therapy of humans and animals, and other areas where fast thermocycling is needed. The therapy in human and animal can be applied internally or externally and can be used for pain reduction, inflammation, and edema of joints, muscles, and nerves. The cryo-heating therapy can be applied to wound healing, injury healing, thrombosis, skin treatment, cosmetic treatment, and other medical applications.

The invention also advances applications of the disclosed herein method to up-conversion energy cooling of electronic components and photon detector devices.

DETAILED DESCRIPTION OF PREFERRED EMBODIMENTS

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon the claimed invention.

This invention discloses novel cryo-heating devices and methods for cooling and heating objects in a very rapid timescale, from femtoseconds to sub-seconds. The timescale of cooling and heating processes depends mainly on the rates of absorption and up-conversion energy of an up-converting energy medium, where the rates can range from femtoseconds to subseconds for up-converting energy organic dyes and up-converting energy phosphors, respectively. The selection of the up-converting energy medium in the proposed cryo-heating device depends on the application. The invention also includes cryo-heating devices and methods for cooling and heating of objects/molecules within timescales of seconds to hours.

Figure 1:
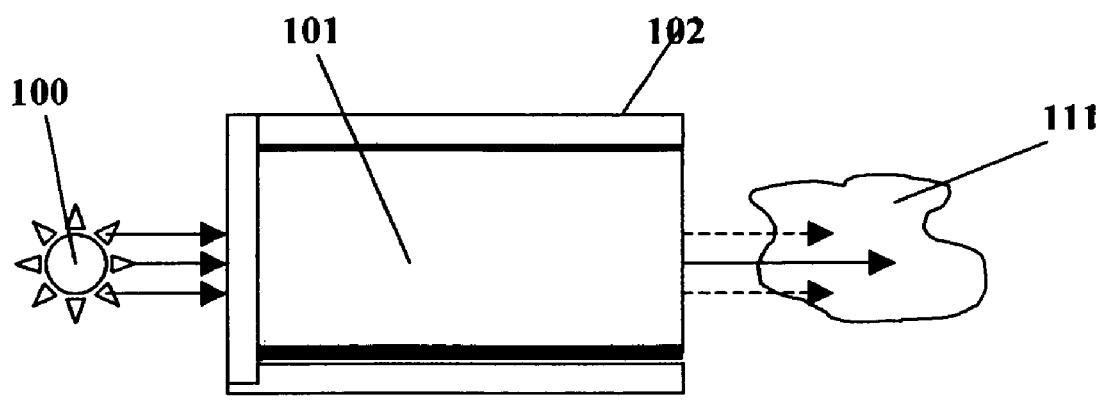
FIG. 1. A head of a cryo-heating device
Figure 2A:
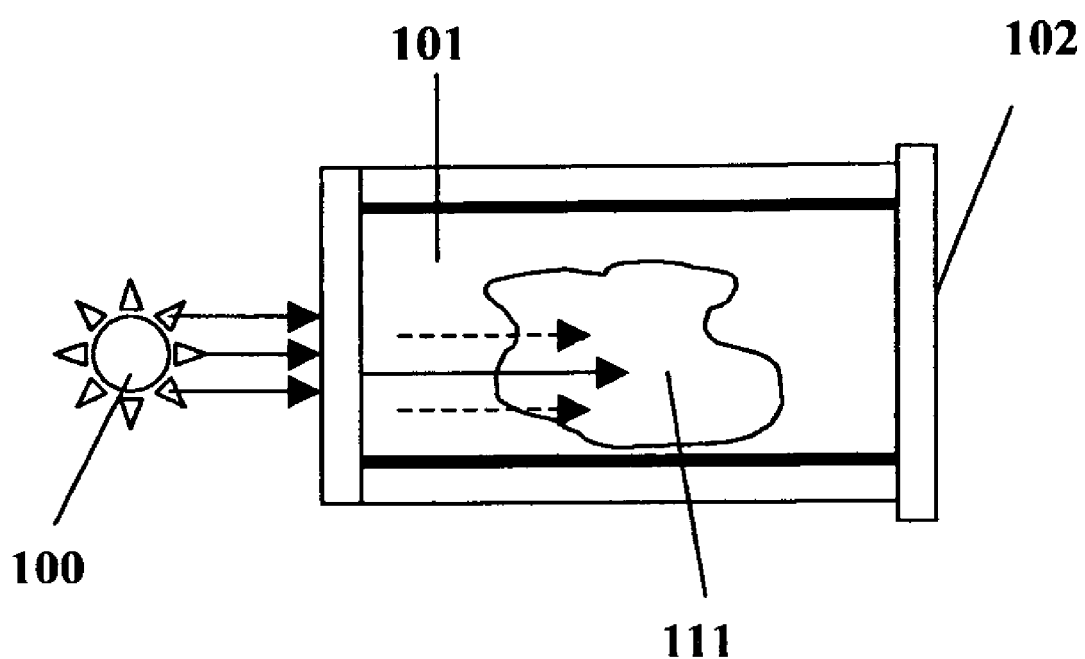
FIG. 2. A head of a cryo-heating phototreatment device with non-contact heating and cooling capabilities FIG. 3. A head of a cryo-heating device with conducting nanostructures placed in the medium as a colloidal suspension FIG. 4. A head of a cryo-heating device with conducting nanostructures attached to inner walls of a housing FIG. 5. An elastic bandage with an array of LEDs and with a supporting thermal energy source for cooling and heating FIG. 6. An elastic bandage with an array of laser diodes and with a supporting thermal energy source for cooling and heating FIG. 7. A hand-held cryo-heating device FIG. 8. A catheter as a cryo-heating device FIG. 9. An endoscope as a cryo-heating device FIG. 10. An up-conversion cooling of an IC processor FIG. 11. An up-conversion cooling of a photodetector to reduce a photodetector thermal noise
Figure 2B:
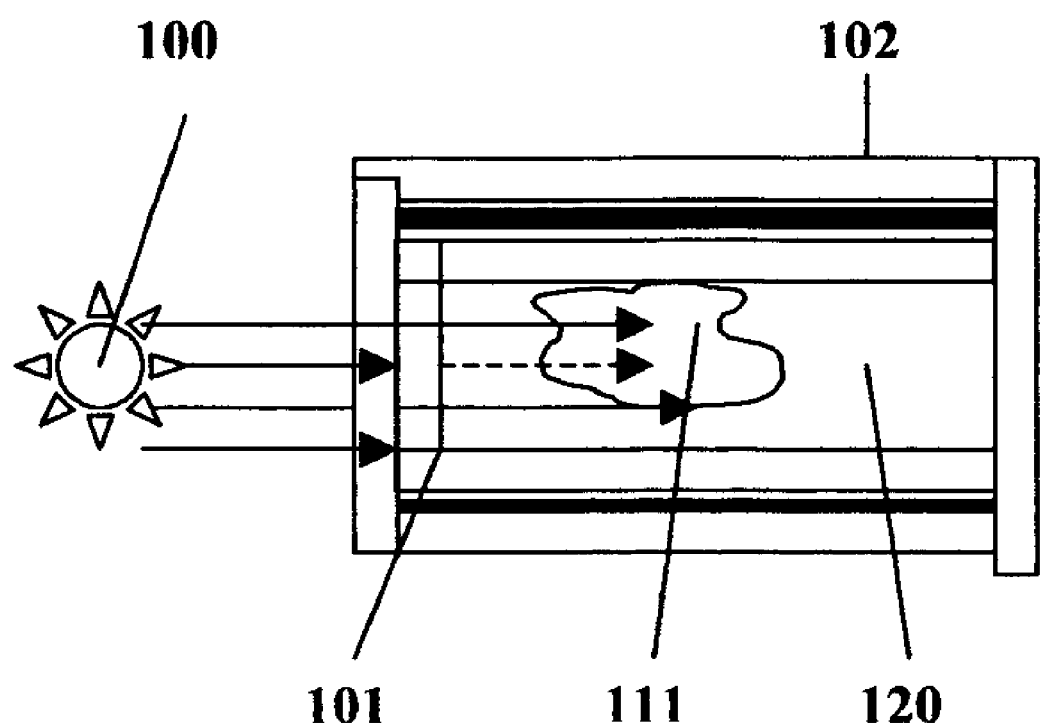

An example of a cryo-heating device is shown in FIG. 1. The device is comprised of an electromagnetic radiation source 100 with an up-converting energy medium 101, and housing 102. The electromagnetic radiation source 100 illuminates medium 101 to cool or heat the medium that subsequently cools or heats object 111. The object 111 can also be placed inside the head, in medium 101 (FIG. 2a) or in buffer 120 (FIG. 2b), which allows for direct heating and cooling of object 111 by medium or by buffer 120, respectively.

The invention considers the cooling and heating of objects at the same time or at different times. In the latter case, cooling and heating can be performed in a cycle, often called "thermocycle". A cycle rate can be selected from femtoseconds to hours. However, some applications may benefit when cooling and heating of objects are performed simultaneously. As it is known, the rate of cooling by conduction is lower than the rate of electromagnetic heating. Therefore, the simultaneous use of both processes can generate a gradient temperature in the object, which may have a myriad of values.

The invention considers the use of the same wavelength or different wavelengths for cooling and heating. The latter option provides better flexibility in designing phototreatments. For example, in the polymerase chain reaction application, it is important to select wavelengths of electromagnetic radiation for the best heating and cooling that correspond to the highest absorption coefficient of water and the highest up-converting energy of medium, respectively.

Figure 3:
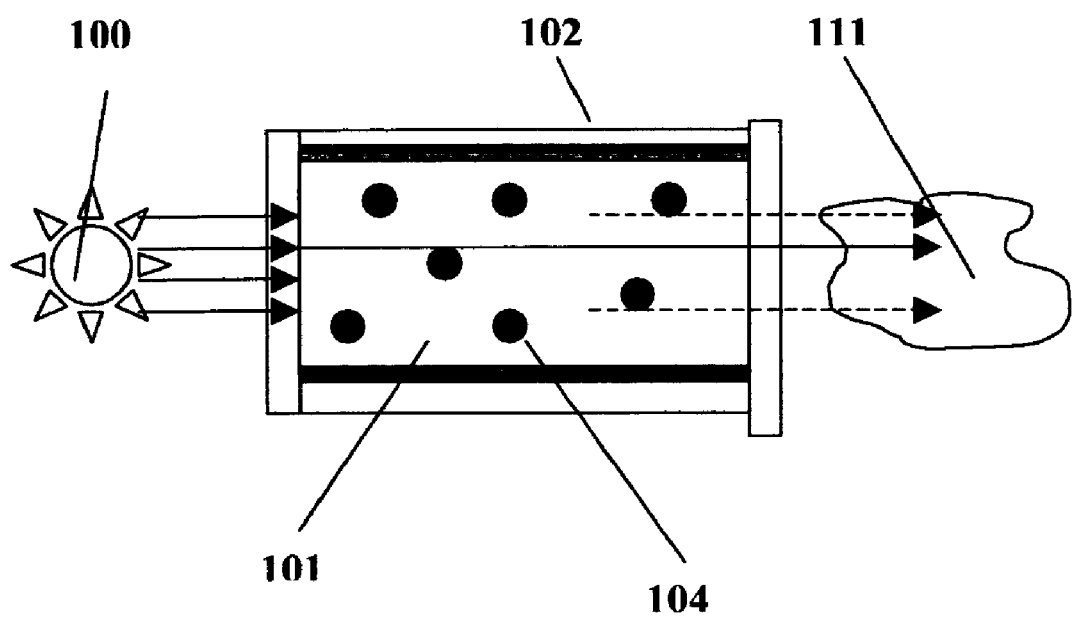
Figure 4:
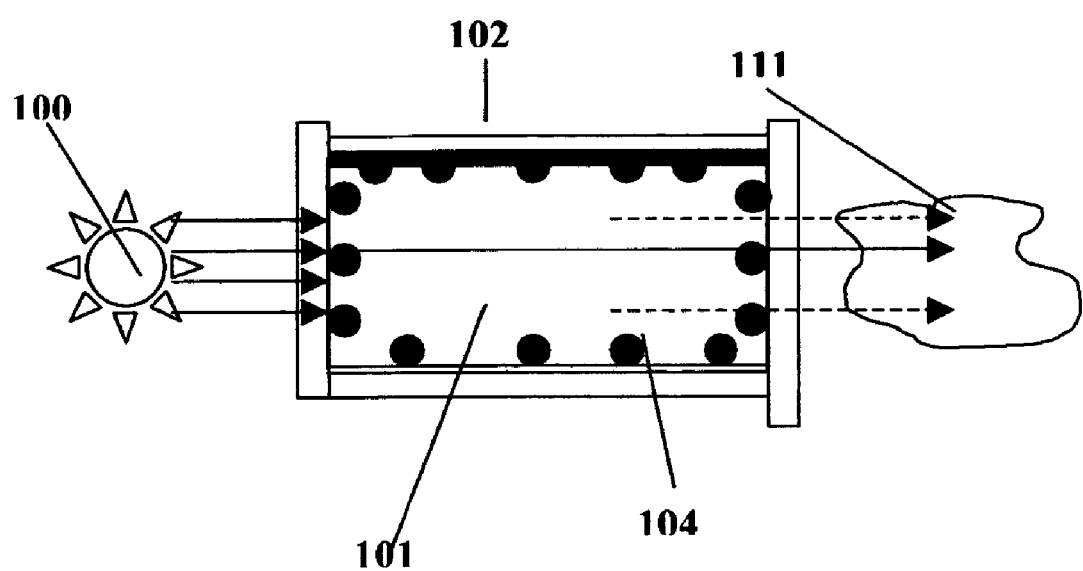

Anyone skilled in the art would appreciate the use of conducting nanostructures to enhance cooling and heating processes in the up-converting energy medium. The nanostructures may play multiple roles in this enhancement. They will increase absorption rates of up-converting substances and they will very effectively conduct heat to up-converting substances, which in both cases lead to enhanced cooling and/or heating of objects, respectively. Nanostructures 104 can be placed in medium 101 as a colloidal suspension (FIG. 3) or can be attached to the inner walls of housing 102 (FIG. 4). The nanostructures can also be coated with dielectric or other materials to eliminate potential quenching of up-conversion energy in the medium.

The cooling and heating processes induced by electromagnetic radiation in the proposed cryo-heating device can be supported by at least one additional energy source selected from the group of sonic, magnetic, electric, electroluminescent, microwave, luminescence, pressure, and thermal. Use of these supporting sources depends on the application. For example, cooling and heating of a microliter or smaller volume object can be performed with an electromagnetic source, but objects of larger volumes may need the support of other energy sources for cooling and heating, particularly if there is a requirement for rapid thermocycling. The supporting energy sources can be designed for specific applications, such as, the design of sonic or microwave energy sources as focused energy sources that deliver their energy to the same location as the electromagnetic radiation.

The electromagnetic radiation source and the supporting sources can be used as linear or nonlinear energy sources. Nonlinearity of the energy sources may provide three-dimensional resolution capabilities for cooling and heating of objects.

Figure 5:
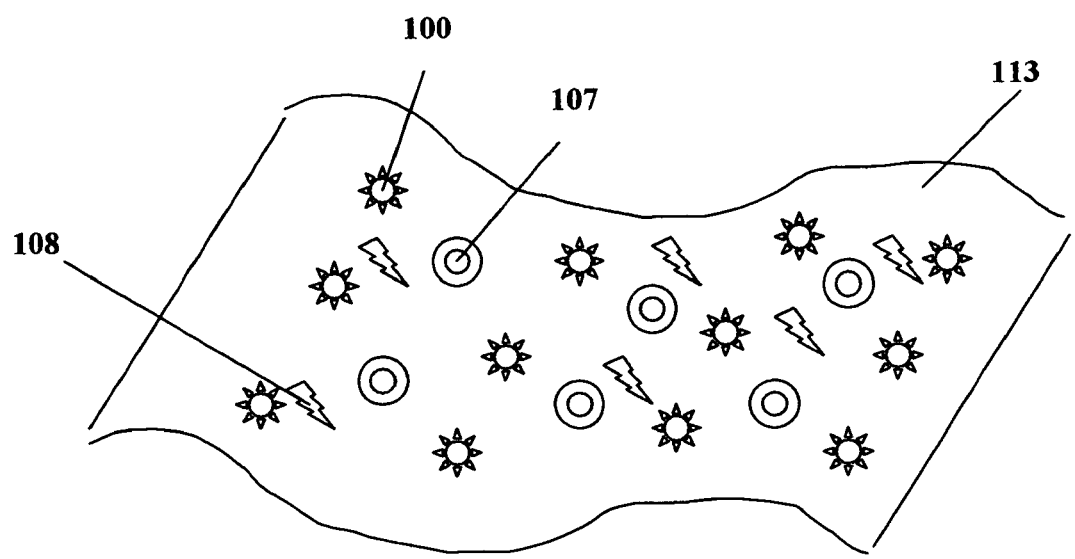
Figure 6:
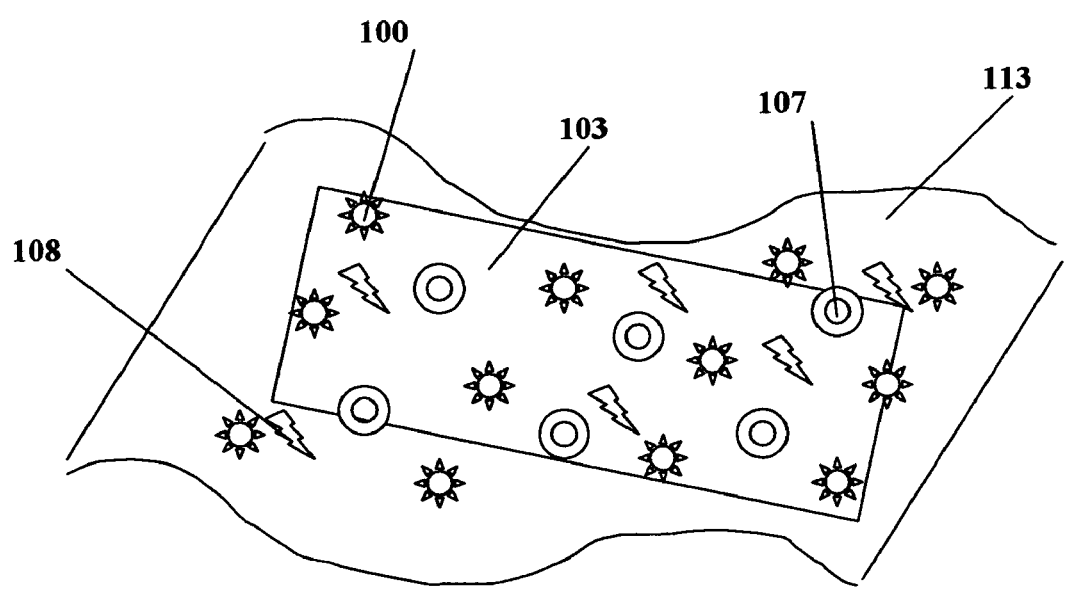
Figure 7:
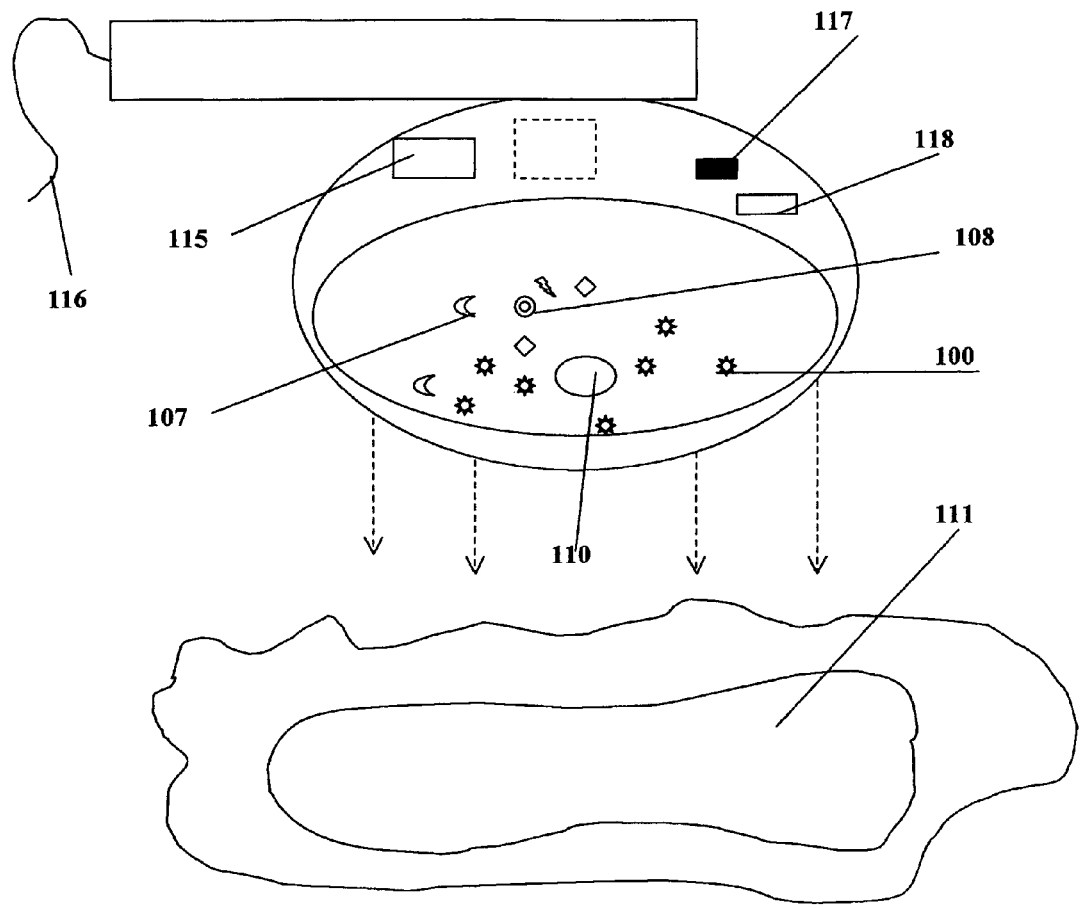

The proposed cryo-heating phototreatment device can be designed as a stand-alone device or a portable device. Exemplary designs of the portable devices are shown in FIGS. 5-9. FIGS. 5 and 6 show an elastic bandage in which electromagnetic source 100 is an array of LEDs or an array of laser diodes, and the supporting thermal energy sources for cooling 107 and heating 108, respectively. The up-converting medium 101 is assembled together with the electromagnetic source 100 (FIG. 5) or thin film 103 is placed on top of electromagnetic source 100 (FIG. 6). Depending upon the application, the other supporting energy sources can be implemented into this elastic bandage device or to other cryo-heating devices. FIG. 7 shows a hand-held cryo-heating phototreatment device. The device can be applied internally or externally to any part of the body including nerve sites.

Figure 8:
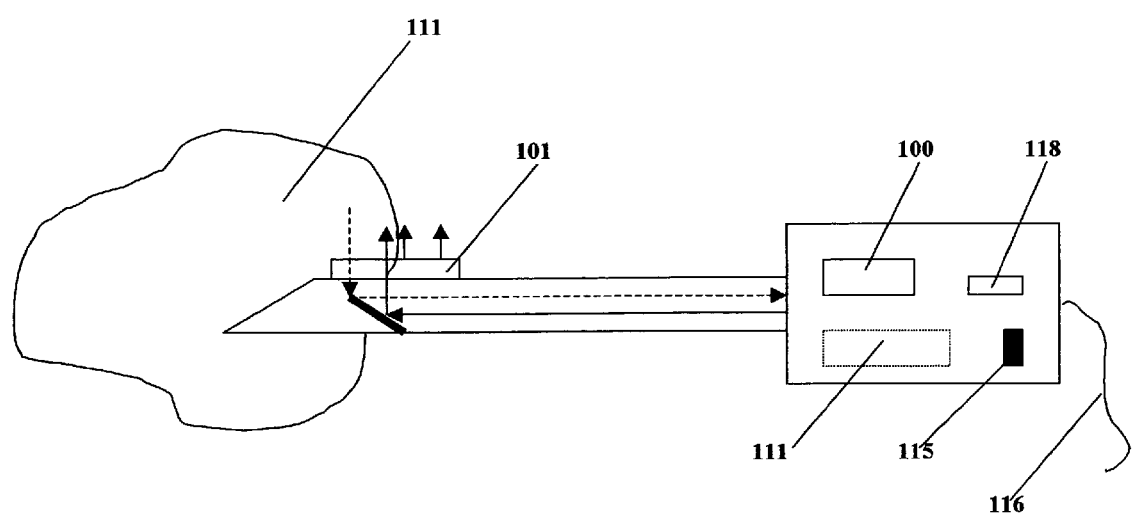
Figure 9:
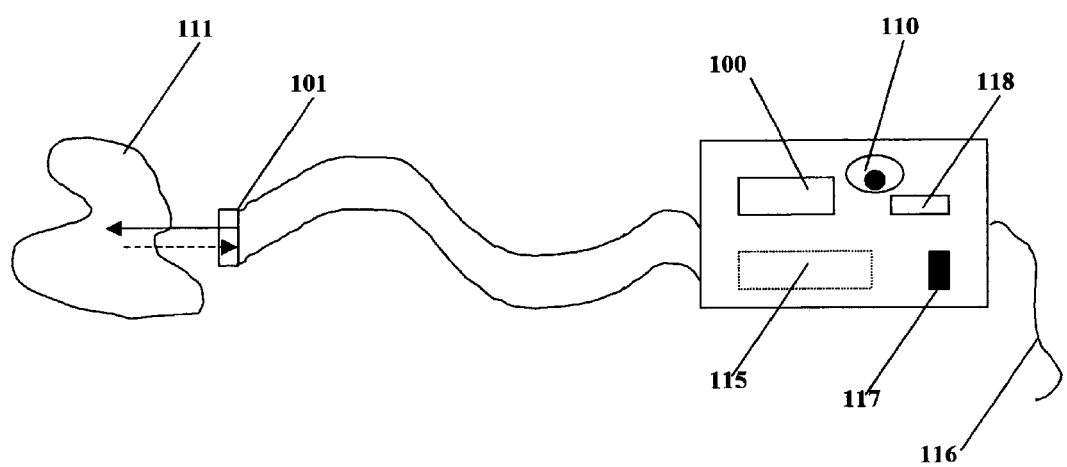

A catheter and endoscope as cryo-heating phototreatment devices are shown in FIGS. 8 and 9, respectively. These devices will be used internally for phototreatment, detection, and manipulation of biomaterials, such as proteins, DNA, cells, tissue, and body fluids. The capabilities of cooling and heating internal biomaterials with the proposed device will reveal new areas of the application, for example, the biostimulation of cells by thermocycling, amplification of genetic material in vivo and in vitro, freezing biomaterials in vivo and in vitro, instantaneous cooling in surgery of the surgical site to minimize inflammation or bleeding.

Another embodiment of the invention is related to sensory feedback 110 that is incorporated into the cryo-thermal device. The sensory feedback may monitor in real-time biometrics of the cooled and/or heated objects and inform central unit 109 of the device about the occurring phototreatment. Central unit 109 may process this information and change parameters of the device or phototreatment program to optimize the phototreatment. The central unit can be preprogrammed and a medical doctor, technician, or patient may select a specific program for the treatment. The doctor, technician, or patient can also remotely control the device. The feedback may also serve as a real-time controller of the device performance. Sensory feedback 110 may comprise different types of sensors for measuring biochemical and physical parameters of the cooled or heated objects. The sensors may also include imaging sensors to provide images of the treated object.

The cryo-heating device may comprise of the following major components: multiplex energy source 112 assembled on substrate 125, drive circuit in electrical connection 114 with multiplex energy source 112, programmable electronics 113, said sensory feedback 110, communication unit 115 and power supply 116 with on/off switch 117, and custom-designed software and computer 118.

One of the embodiments of this invention proposes to apply the cryo-heating phototreatment device to phototherapy of humans and animals. The cryo-heating therapy can be used internally or externally to the body for reducing pain, inflammation, edema of joints, muscles and nerves. The cryo-heating therapy can also be applied to wound healing, reducing thrombosis, skin treatment, acupuncture therapy, cosmetic treatment, sport injury, and other medical applications.

Anyone skilled in the art will appreciate the use of the cryo-heating device with the pulsed/modulated radiation sources. The proposed device benefits from a broadband range of frequencies that allow for better design of the device for a variety of applications. For example, the electromagnetic radiation pulsing or modulating at THz frequencies will very effectively deposit thermal energy within the object. Therefore, at these high frequencies, there would not be a need for the matching of absorption properties of the object with wavelengths of electromagnetic energy. In common cases of use of pulsed/modulated energy sources at lower frequencies, where emitted wavelengths or energies of the device are matched with absorption energy properties of the object, the object benefits more from the absorption of pulsed/modulated radiation energies than from continuous energies, particularly if the object is a living body. The pulsed/modulated radiation sources are also more compact than continuous sources, and can be used in cryo-heating portable devices, such as an elastic bandage device, hand-held device, but not limited to them. Regarding pulse duration in the cryo-heating devices, the invention considers pulses generated by the energy sources within a range of the pulse duration from femtoseconds to seconds. This widespread range of the pulse durations is dictated by up-converting media. For example, femtosecond to nanosecond pulses are preferable for cooling processes with up-converting energy organic dyes, and subseconds to seconds pulses are preferable for cooling processes with up-converting energy phosphors and rare earth elements.

Figure 10:
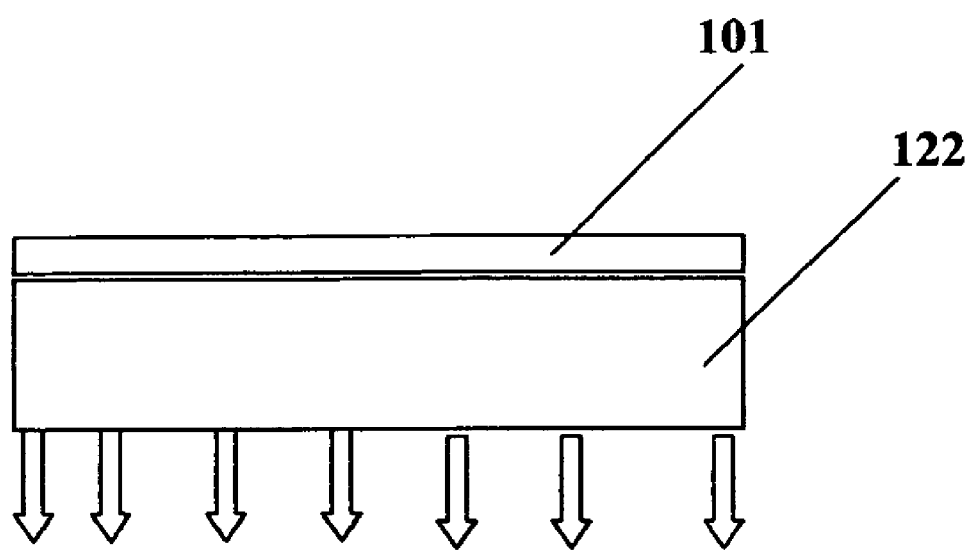
Figure 11:
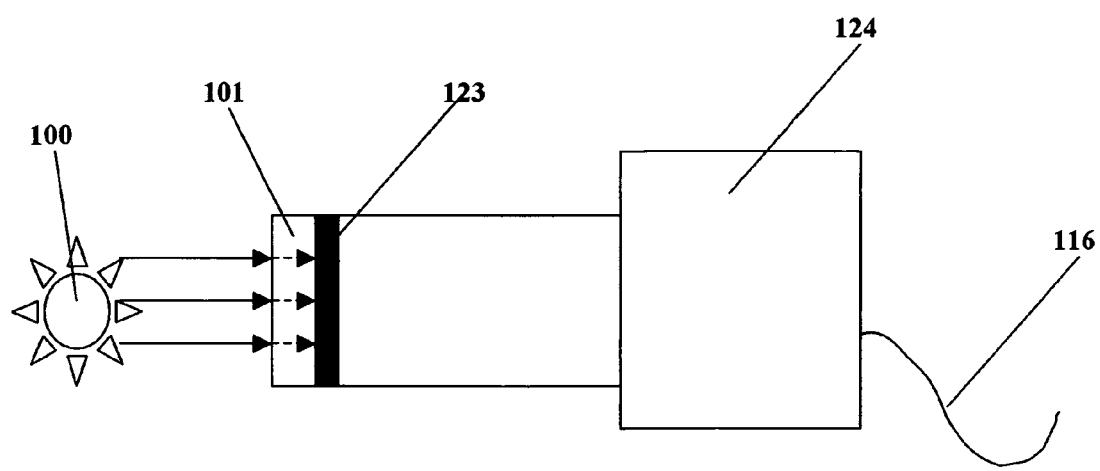

Another embodiment of the invention is related to cooling electronic components with up-conversion energy processes. For example, as is shown in FIG. 10, the back of IC processor 122 may have an additional layer of up-converting medium 101 that under electromagnetic excitation will luminesce and cool down the IC processor. The process of up-conversion energy cooling of the IC chip can be very effective, because of excessive heat generated by the IC chip. The up-conversion energy cooling processes can also be applied to photon detector technology. Photosensitive element 123 in photodetector 124 can be coated with up-converting medium 101 and under electromagnetic illumination (FIG. 11), the up-converting medium will generate photons and at the same time will cool the photosensitive elements. This leads to a reduction of thermal noise of the photodetector. This effect will be more pronounced in the detectors with relatively small photosensitive elements, such as micro-channel plates, nano-channel plates, pin diodes, 2D array detectors: CCD, CMOS. In the proposed method, it is also possible to use wavelengths insensitive to the photodetector for the up-conversion energy cooling, which would allow for no interference in the functioning of the photodetector at different wavelengths. This way the range of spectral sensitivity of the detector can be extend. The photodetector can be selected from the group consisting of photomultiplier, photodiode, micro-channel plate, nano-channel plate, CCD chip, CMOS chip and other photosensitive electronics.

What is claimed is:

1. A method of rapid repeated cooling and heating of molecules by up-converting energy medium comprising steps of: providing a molecule to be cooled and heated; providing an up-converting energy medium, wherein the up-converting energy medium is capable of being cooled by electromagnetic radiation at wavelength 1 and heated by electromagnetic radiation at wavelength 2; providing an electromagnetic source capable of radiating electromagnetic radiation at wavelength 1 and at wavelength 2; contacting the molecule with the up-converting energy medium; irradiating the up-converting energy medium with electromagnetic radiation at wavelength 1 to cool the molecule by the up-converting energy medium; irradiating the up-converting energy medium with electromagnetic radiation at wavelength 2 to heat the molecule by the up-converting energy medium; irradiating the up-converting energy medium with electromagnetic radiation at wavelength 1 to cool the molecule by the up-converting energy medium; and irradiating the up-converting energy medium with electromagnetic radiation at wavelength 2 to heat the molecule by the up-converting energy medium.

2. The method of claim 1, wherein said the molecule is selected from the group of: a genetic material, biomolecule, cell, tissue, skin, joint, nerve, meridian, body fluid, plant, food, microbe, or fungi.

3. The method of claim 1, wherein said electromagnetic source is radiating electromagnetic radiation at a wavelength range from ultraviolet to microwave.

4. The method of claim 1, wherein said electromagnetic source is a continuous radiation source or a pulsed radiation source.

* * * * *